(12) United States Patent
Kurrus

(10) Patent No.: US 8,181,558 B2
(45) Date of Patent: May 22, 2012

(54) SHAPING DEVICE

(75) Inventor: Michael R. Kurrus, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 499 days.

(21) Appl. No.: 12/386,795

(22) Filed: Apr. 23, 2009

(65) Prior Publication Data

US 2009/0265941 A1   Oct. 29, 2009

Related U.S. Application Data

(60) Provisional application No. 61/125,284, filed on Apr. 24, 2008.

(51) Int. Cl.
*B26D 5/08* (2006.01)
*A61M 25/14* (2006.01)

(52) U.S. Cl. ............................... 83/597; 30/92; 604/523

(58) Field of Classification Search .................... 83/597, 83/598, 599, 604, 644, 647, 578, 693, 694; 30/92, 242, 113, 494, 94, 184, 182, 186, 30/181, 272.1; 74/469; 604/523
See application file for complete search history.

(56) References Cited

U.S. PATENT DOCUMENTS

| | | | | |
|---|---|---|---|---|
| 1,697,434 A | * | 1/1929 | Moore, Jr. ..................... | 83/861 |
| 6,473,972 B1 | * | 11/2002 | Guerin ............................ | 30/181 |
| 2003/0047052 A1 | * | 3/2003 | Merritt ........................... | 83/599 |
| 2003/0084772 A1 | * | 5/2003 | Shen .............................. | 83/597 |

* cited by examiner

*Primary Examiner* — Stephen Choi
(74) *Attorney, Agent, or Firm* — Brinks Hofer Gilson & Lione

(57) ABSTRACT

An elongate element, in particular a catheter, has a curved shape imparted to its end by a device comprising razor blades which are mounted on a pivotal linkage mechanism. Upon pressing actuator members against the restoring force of spring elements, the razor blades are constrained by the pivotal linkage mechanism to follow a desired curved path.

8 Claims, 2 Drawing Sheets

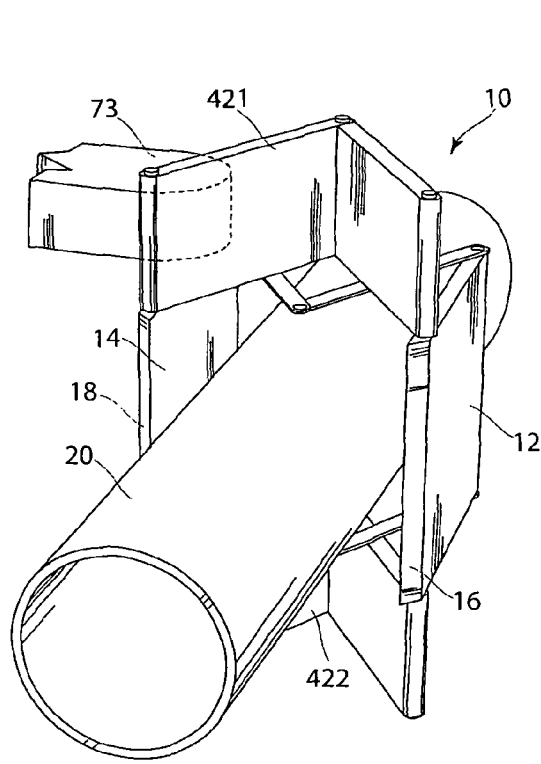
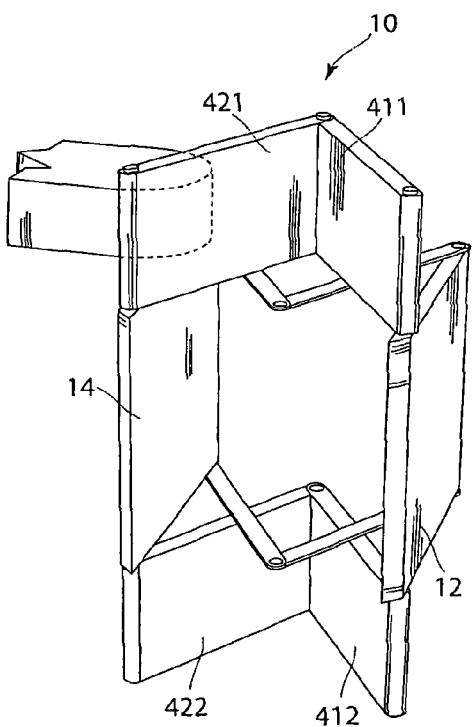
FIG. 5
FIG. 6
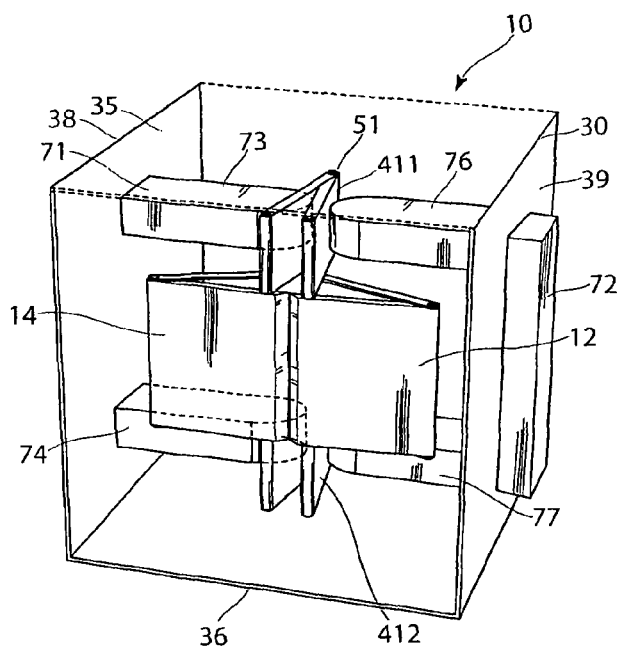
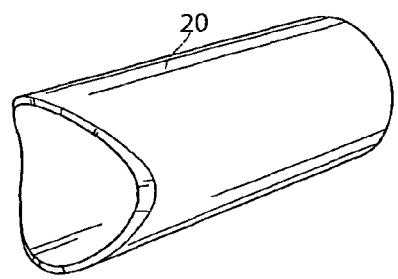
FIG. 7
FIG. 8

SHAPING DEVICE

CROSS-REFERENCE TO RELATED APPLICATIONS

This application claims priority of provisional application Ser. No. 60/125,824, filed Apr. 23, 2008.

TECHNICAL FIELD

The present invention relates to a shaping device and more particular to a device for cutting an end of an elongate member to impart it to a desired curved shape. In preferred embodiments of the present invention an end of a catheter is shaped.

BACKGROUND OF THE INVENTION

It is known to manufacture catheters with soft tips. However, in cases where there is a need to trim a catheter to fit an individual patient's anatomy, such as a PICC (peripherally inserted central catheter), this leaves a relatively hard and untrimmed tip which is traumatic for the patient during insertion of the catheter. PICC catheters are used for the intravenous administration of nutrient fluids, chemotherapeutic agents and other drugs for therapy.

Aspects of the present invention seek to reduce or overcome the above problem.

SUMMARY OF THE INVENTION

According to a first aspect of the present invention there is provided a device for imparting a curved shape to an end of an elongate element, the device comprising a support member and at least one cutting member mounted on the support member to move relatively thereto, the cutting member being connected to the support member by means of a pivotal linkage mechanism, the pivotal linkage mechanism constraining the cutting member to move along a path to define said curved shape as it moves, and at least one actuating member arranged to cause said movement of the cutting member.

According to a second aspect of the present invention, there is provided a device for cutting a desired curved shape in the end of a catheter comprising a housing, a first member having a first, cutting end and a second end, a second cutting member having a first, cutting end and a second end, a pivotal mechanism located in said housing and comprising first, second, third and fourth links, said first and second links being pivotally connected by a first pivot element, said first pivot element being fixed to said housing, said third and fourth links being pivotally connected by a second pivot element, said second pivot element being slidably mounted in said housing, said first link being pivotally connected by a third pivot element to said first end of said first cutting member, said third link being pivotally connected by a fourth pivot element to said second end of said first cutting member, said second link being pivotally connected by a fifth pivot element to said first end of said second cutting member, and said fourth link being pivotally connected by a sixth pivot element to said second end of said second cutting member, a first actuating member arranged to slide relative to said housing from a first position to a second position, said first actuating member engaging said first link to cause movement of said first cutting member to impart said desired curved shape to the catheter, a second actuating member arranged to slide relative to said housing from a first position to a second position, said second actuating member engaging said second link to cause movement of said second cutting member to impart said desired curved shape to the catheter, a first resilient member for returning said first actuating member from its second position to its first position, and a second resilient member for returning said second actuating member from its second position to its first position.

According to a third aspect of the present invention, there is provided a catheter having a longitudinal axis and an end which is of curved shape viewed in directions perpendicular to the longitudinal axis.

BRIEF DESCRIPTION OF THE DRAWINGS

Preferred embodiments of the present invention will now be described, by way of example only, with reference to the accompanying drawings of which:

FIG. 5 is a perspective partial view of the operating mechanism of the device of FIG. 1 in its initial disposition and with an inserted catheter;

FIG. 6 is a view similar to FIG. 5 but without the catheter;

FIG. 7 is a view similar to FIGS. 5 and 6 of the device of FIG. 1 in its end position and showing the housing; and FIG. 8 shows the end of a catheter cut by the device.

DETAILED DESCRIPTION

Figure 1:
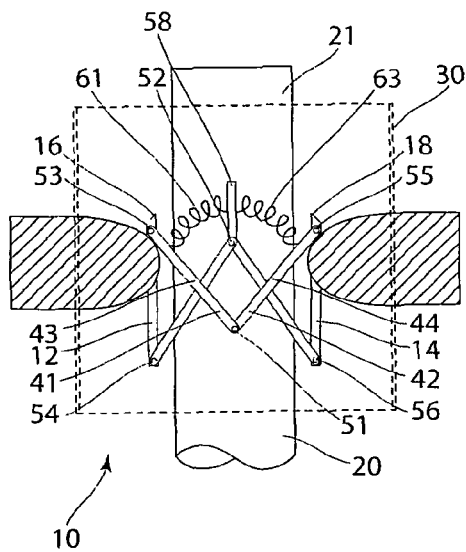
FIG. 1 is a sectional view of an embodiment of a shaping device in an initial disposition and showing an inserted catheter to be trimmed.
Figure 4:
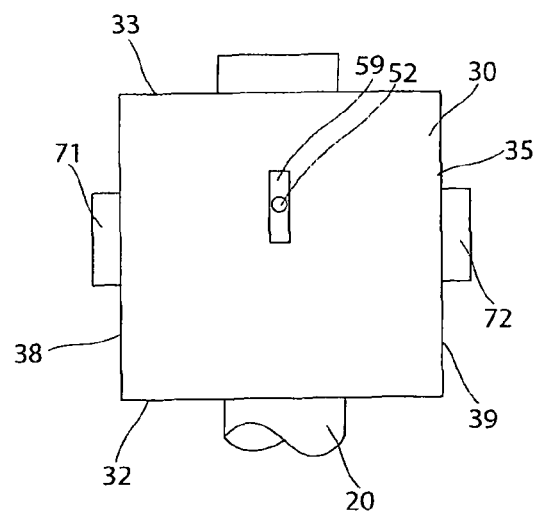
FIG. 4 is an external view of the device of FIG. 1, showing the housing thereof.

Referring to the drawings, FIG. 1 shows a sectional view of a cutting device 10 for shaping the end of a catheter 20, typically of a plastics material. The device has a housing 30, shown only in section in FIG. 1, having open ends 32, 33 (FIG. 4) through which the catheter end 21 to be trimmed is passed. Device 10 comprises two razors 12,14 having respective cutting edges 16, 18. The razors have blunt edges at their ends opposite to cutting edges 16, 18. The razors are interconnected by a linkage mechanism 40 comprising four links 41-44 connected to each other and to the razors 12, 14 by six pivotal connections at pivot pins 51-56.

Links 41 and 42 are interconnected by pivot pin 51 so as to pivot relatively to each other. The ends of pivot pin 51 are fixedly attached to housing 30. Links 43 and 44 are interconnected by pivot pin 52 so as to pivot relatively to each other. The ends of pivot pin 52 are attached to respective bearings 58 which slide in respective slots 59 arranged in the top 35 and bottom 36 of housing 30. Thus pivot pin 52 is constrained to move in a direction parallel to the length of the catheter 20.

The other ends of links 41 and 42 are respectively connected by pivot pins 53, 55 to razors 12, 14 adjacent the sharp edges thereof. The other ends of links 43 and 44 are respectively connected by pivot pins 54, 56 to razors 12, 14 adjacent the blunt edges thereof. A coil spring 61 is connected between link 41 and bearing 58. A coil spring 63 is connected between link 42 and bearing 58. In the initial disposition of the device shown in FIG. 1, the springs 61 and 63 are relatively relaxed.

As can be seen from FIGS. 5 to 7, links 41, 42 are in the form of plate members with ends 411, 412 and 421, 422 extending above and below the rest of the operating mechanism. The sides 38, 39 of housing 30 have apertures therein for slidably retaining respective actuator members 71, 72.

Actuator member 71 comprises upper and lower projecting fingers 73, 74 which respectively engage the upper and lower ends 421 and 422 of link 42. In mirror image fashion, actuator member 72 comprises upper and lower projection fingers 76, 77 which respectively engage the upper and lower ends 411, 412 of link 41.

The lengths of links 4144 and the position of pivot pins 51 to 56 are selected so that the razor edges 16, 18 can move to sever the end of 20 leaving an end of a desired curved shape or contour. This is achieved as follows.

Figure 2:
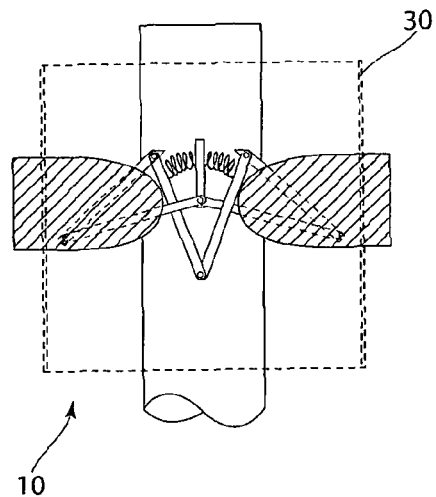
FIG. 2 is similar sectional view of the device of FIG. 1 in an operating disposition thereof.

Catheter 20 is first inserted through the open ends 32, 33 of housing 30 until the desired cutting location along the length of the catheter lies within the housing. Actuator members 71, 72 are then manually urged towards each other so that straight cutting edges 16, 18 engage the catheter 20 at the precise location where it is desired to commence cutting. It will be appreciated that the members 71, 72 act in substantially mirror-symmetrical fashion. As the actuator members are pushed closer together, cutting commences and the material of the wall of the catheter is cut as the edges 16, 18 move from the relative disposition in FIG. 1 to that shown in FIG. 2. Initially each blade edge cuts material from a single region of the catheter wall, but as cutting continues, each blade subsequently cuts the wall at two spaced locations (above and below the plane of the paper in FIGS. 1 and 2). There thus results a cut which is curved in three dimensions. During the cutting movement, the cutting edges 16, 18 cover the path indicated by line 19 in FIG. 3, which corresponds to the shape of the cut edge in the plane of the drawing.

During the movement of the actuator members, pivot pin 52 on bearing 58 is able to slide parallel to the length of the catheter. Also, pivot pins 53, 54 are moved towards each other so that springs 61, 63 are compressed between links 41, 42 respectively and bearing 48.

Figure 3:
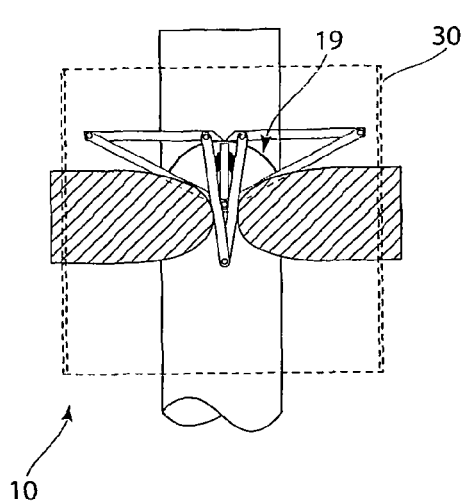
FIG. 3 is a similar sectional view of the deice of FIG. 1 in an end disposition thereof.

Finally, actuator members 71, 72 reach their closest portion, FIG. 3, in which cutting edges 16, 18 meet and the cutting operation is complete. The actuator members are then released and the springs 61, 63 push links 41, 42 so that the operating mechanism returns to the disposition shown in FIG. 1 and the cut catheter can be removed from the housing.

The resulting saddleback shape of the end of the catheter 20 is shown in FIG. 8.

An advantage of the above-described device is that it enables a non-traumatic catheter tip to be quickly and easily produced. This is particularly advantageous should the need arise, perhaps unexpectedly during a surgical operation. If it is found that a catheter has been cut to the wrong length, it can quickly be cut again.

It will further be appreciated that the cutting procedure produces a trauma-free profile on both sides of the cut. Thus both parts of the cut catheter could be used in medical procedures.

Numerous modifications can be made to the above-described device.

For example, coil springs corresponding to coil springs 61, 63 can also be provided at the bottom of housing 30. The springs could be configured to be tensioned instead of compressed by operation of the device, before returning to the initial disposition. The springs may be replaced by other suitable resilient members. Alternatively, no resilient members are provided in which case the cutting members are returned manually by the user to their initial disposition.

An arrangement comprising a bearing 58 and a slot 59 may be provided only at the top or bottom of the housing 30 instead of at both locations. Pivot pin 51 may be arranged to slide relative to the housing.

Although relatively simple actuator members 71, 72 in the form of push buttons are described in connection with above embodiment, these may be modified as desired. For example they may have handles and/or their own further linkage mechanism to enable a higher force to be exerted on the cutting edges, e.g. for catheters of relatively hard material. Instead of being generally cuboidal, housing 30 can be cylindrical. Alternatively, housing 30 can be omitted, in which case a framework is provided for mounting at least pivot pins 51 and 52. The framework can include means for guiding the members 71, 72. Alternatively the actuator members may have no guiding means. In a further modification, the actuator member can be omitted and the ends 411 and/or 412 are directly moved manually. The lengths and points of connection of the various links, and even the number of links, may be varied to provide a desired cut shape. For example, it may be desired to produce a shape which has a greater curvature in some regions and a lesser curvature or no curvature in other regions. The shape of the cutting edges 16, 18 may also be selected as desired.

Additional means (not shown) may be provided for retaining an inserted catheter within the housing or framework before cutting commences.

In another modification, a device with only a single blade is provided. First one half of the total cut is made, the catheter is then rotated around its axis by 180° and then the cut is completed by severing the remaining half of the catheter. Although such a device is not so quick and convenient s the above-described device, it requires fewer components and is thus cheaper.

If the catheter is of a relatively soft plastic material, a mandrel (e.g. of steel) may be placed inside the catheter to stiffen it adjacent the region to be cut. Curved razor edges can be used here to avoid contact with the internal mandrel.

The catheter to be cut may have a circular, elliptical or other cross-sectional shape.

The catheter to be cut may have two or more lumens. By rotating the catheter during the cutting process, different tip configurations can be obtained; this offers possibilities for reducing vessel trauma and thrombosis problems.

The device may be used to cut any elongate object, whether of hollow or solid cross-sectional shape, to any desired end profile.

The features of the various modifications may be combined or substituted as desired.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims—and their equivalents—in which all terms are meant in their broadest reasonable sense unless otherwise indicated.

What is claimed is:

1. A device for imparting a curved shape to an end of an elongate tubular element, the device comprising a support member and at least one cutting member mounted on the support member to move relatively thereto, the cutting member being connected to the support member by means of a pivotal linkage mechanism, the pivotal linkage mechanism constraining the cutting member to move along a path to define said curved shape as said cutting member moves relative to the support member, said curved path intersecting a longitudinal axis of the elongate tubular element, and at least one articulating member arranged to cause said movement of the cutting member, wherein the cutting member is an elongate member having a first cutting end and a second non-cutting end that is opposite the first cutting end, and said pivotal linkage mechanism comprises a plurality of links connected to said cutting member at spaced apart locations by a plurality of pivot elements.

2. A device according to claim 1, wherein at least one of said plurality of links is connected to the support member.

3. A device corresponding to claim 2, wherein a first of said plurality of links is pivotally connected to the support member, and a second of said plurality of links is slidingly connected to the support member, said sliding connection being movable along an axis parallel to the longitudinal axis of the elongate element.

4. A device according to claim 2, wherein the first cutting end of the cutting member is connected to a first link and the second non-cutting end of the cutting member is connected to a second link, and said actuating member is arranged to engage said first link so as to move said cutting member along said curved path.

5. A device according to claim 1, wherein said pivotal linkage mechanism comprises a resilient element acted upon by said actuating member as the pivotal linkage mechanism causes said movement of the cutting member from an initial disposition, said resilient member being arranged, upon release of said actuating member, to return said actuating member and the cutting member to the initial disposition.

6. A device according to claim 1 comprising two cutting members arranged in a substantially mirror symmetrical manner to cut said elongate element from opposite sides.

7. A device for cutting a desired curved shape in the end of a catheter comprising a housing, a first member having a first, cutting end and a second end, a second cutting member having a first, cutting end and a second end, a pivotal mechanism located in said housing and comprising first, second, third and fourth links, said first and second links being pivotally connected by a first pivot element, said first pivot element being fixed to said housing, said third and fourth links being pivotally connected by a second pivot element, said second pivot element being slidably mounted in said housing, said first link being pivotally connected by a third pivot element to said first end of said first cutting member, said third link being pivotally connected by a fourth pivot element to said second end of said first cutting member, said second link being pivotably connected by a fifth pivot element to said first end of said second cutting member, and said fourth link being pivotally connected by a sixth pivot element to said second end of said second cutting member, a first actuating member arranged to slide relative to said housing from a first position to a second position, said first actuating member engaging said first link to cause movement of said first cutting member to impart said desired curved shape to the catheter, a second actuating member arranged to slide relative to said housing from a first position to a second position, said second actuating member engaging said second link to cause movement of said second cutting member to impart said desired curved shape to the catheter, a first resilient member for returning said first actuating member from said second position to said first position, and a second resilient member for returning said second actuating member from said second position to said first position.

8. A device according to claim 7, wherein said housing comprises a wall having a slot therein and said second pivot element is connected to a bearing arranged to slide in said slot, and wherein said first and second resilient members are coil springs connected between said first and second links respectively and said bearing.

* * * * *